(12) United States Patent
Paingankar et al.

(10) Patent No.: US 7,141,697 B2
(45) Date of Patent: Nov. 28, 2006

(54) PROCESS FOR THE PREPARATION OF PHENETHYLAMINE DERIVATIVES

(75) Inventors: Niranjan Paingankar, Mumbai (IN); Vilas N. Mumbaikar, Mumbai (IN); Vadiraj S. Ekkundi, Mumbai (IN); Hans-Peter Jalett, Dornach (CH); Urs Siegrist, Eiken (CH); Paul Adriaan Van Der Schaaf, Allschwil (CH); Frank Bienewald, Hegenheim (FR); Martin Studer, Basel (CH); Stefan Burkhardt, Gelterkinden (CH)

(73) Assignee: Sandoz AG, Basel (CH)

( * ) Notice: Subject to any disclaimer, the term of this patent is extended or adjusted under 35 U.S.C. 154(b) by 365 days.

(21) Appl. No.: 10/130,196

(22) PCT Filed: Dec. 12, 2001

(86) PCT No.: PCT/EP01/14604

§ 371 (c)(1),
(2), (4) Date: Oct. 15, 2002

(87) PCT Pub. No.: WO02/50017

PCT Pub. Date: Jun. 27, 2002

(65) Prior Publication Data

US 2003/0114711 A1    Jun. 19, 2003

(30) Foreign Application Priority Data

Dec. 20, 2000  (IN) .......................... 1101/MAS/00
May 14, 2001   (IN) .......................... 390/MAS/01

(51) Int. Cl.
    *C07C 211/00*  (2006.01)
(52) U.S. Cl. ..................................... 564/336
(58) Field of Classification Search ................ 564/336
    See application file for complete search history.

(56) References Cited

U.S. PATENT DOCUMENTS

| 3,255,248 A | 6/1966 | Suessenguth et al. ....... 260/563 |
| 4,535,186 A | 8/1985 | Husbands et al. .......... 564/336 |
| 5,266,731 A | 11/1993 | Ayers et al. ............... 564/492 |

FOREIGN PATENT DOCUMENTS

HU        205055       12/1990

OTHER PUBLICATIONS

John P. Yardley et al., Journal of Medicinal Chemistry, American Chemical Society, vol. 33, (1990), pp. 2899-2905.
Tetrahedron 48, 10211-10220 (1992).
John C. Robinson et al., β-Phenylethylamine, Organic Syntheses, Coll. vol. 3, p. 720 (1955) and vol. 23, p. 71 (1943).
Jerry March, Advanced Organic Chemistry, Reactions, Mechanisms, and Structure, Third Edition, p. 815 (1985).
L. Kh. Freidlin and T. A. Sladkova, Catalytic Reduction of Dinitriles, Russian Chemical Reviews, vol. 33 No. 6, pp. 319-330 (1964).

*Primary Examiner*—Samuel Barts
(74) *Attorney, Agent, or Firm*—John Thallemer

(57) ABSTRACT

Disclosed is a process for the preparation of a compound of formula

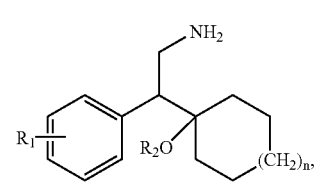

(1)

wherein $R_1$ is hydrogen, hydroxyl, or unsubstituted or substituted alkyl or alkoxy, $R_2$ is hydrogen or a substituent which can be converted to hydrogen, and n is 0, 1 or 2, comprising hydrogenating a compound of formula

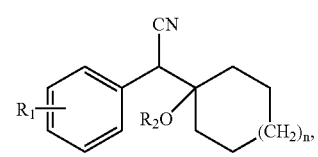

(2)

wherein $R_1$, $R_2$ and n are as defined above, in the presence of a nickel or cobalt catalyst.

16 Claims, No Drawings

PROCESS FOR THE PREPARATION OF PHENETHYLAMINE DERIVATIVES

The present invention is directed to a process for the preparation of phenethylamine derivatives by hydrogenation of phenylacetonitriles in presence of a nickel or cobalt catalyst.

The compounds of formula (1) are known for being particularly useful as synthesis intermediates for preparing pharmaceutical active substances which are central nervous system antidepressants. An important substance is Venlafaxine (see Merck Index Twelfth Edition 1996, No. 10079). The preparation of this compound is described in U.S. Pat. No. 4,535,186.

According to U.S. Pat. No. 4,535,186, Example 2, intermediates of formula (1) are prepared by hydrogenation in the presence of a rhodium catalyst. The use of rhodium catalysts provides economical drawbacks and therefore such catalysts would have to be recycled, resulting in a further process step and the possibility of varying catalytic effect of the recycled catalyst.

It is the object of the present invention to provide a process for the preparation of phenethylamine derivatives in high yields which meets economical demands.

The present invention relates to a process for the preparation of a compound of formula

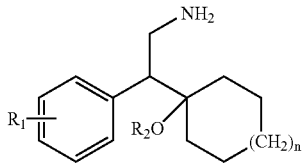

or salts thereof, wherein $R_1$ is hydrogen, hydroxyl, or unsubstituted or substituted alkyl or alkoxy, $R_2$ is hydrogen or a substituent which can be converted to hydrogen, and n is 0, 1 or 2, comprising hydrogenating a compound of formula

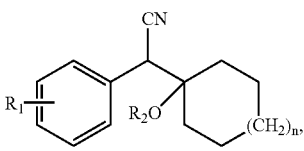

wherein $R_1$, $R_2$ and n are as defined above, in the presence of a nickel or cobalt catalyst.

$R_1$ as alkyl can be a straight-chain or branched alkyl substituent, preferably $C_1$–$C_4$alkyl, such as methyl, ethyl, n-propyl, isopropyl, n-butyl, sec-butyl, tert-butyl. The substituents mentioned can be unsubstituted or substituted. An example for such substituents is phenyl.

$R_1$ as alkoxy can be a straight-chain or branched alkoxy substituent, preferably $C_1$–$C_4$alkoxy, such as methoxy, ethoxy, n-propoxy, isopropoxy, n-butoxy, sec-butoxy, tert-butoxy. Methoxy is preferred. The substituents mentioned can be unsubstituted or substituted. An example for such substituents is phenyl.

Preferably, $R_1$ is hydroxyl or $C_1$–$C_4$alkoxy, especially $C_1$–$C_4$alkoxy. Methoxy is highly preferred. It is preferred that $R_1$ is bonded to the benzene ring in para-position.

Examples for substituents $R_2$ which can be converted to hydrogen are silyl, benzyl, formyl or $C_2$–$C_6$alkanoyl. The conversion can be carried out according to known methods.

Preferably, $R_2$ is hydrogen, formyl or $C_2$–$C_6$alkanoyl, especially hydrogen.

For n the number 1 is preferred.

According to a preferred embodiment of the present invention $R_1$ is methoxy, $R_2$ is hydrogen and n is 1.

According to the present invention nickel or cobalt catalysts well known and used in the hydrogenation field can be used.

For example, a nickel catalyst can be made by thermally decomposing nickel formate or other heat-labile nickel salts, for example in fatty oil, or by precipitating a nickel salt on an inert carrier followed by a reduction with hydrazine or hydrogen gas. A nickel catalyst also can be prepared by the treatment of electrolytically precipitated nickel hydroxide which may be prepared by passing direct current through a cell using nickel as the anode and using the dilute solution of an alkali salt to the weak acid as an electrolyte. The nickel hydroxide so prepared may be conventionally reduced, such as, in the presence of hydrogen gas or hydrazine.

The nickel or cobalt catalyst also may be promoted as is conventional in this field. So, the catalysts may contain, for example, Group VIB metals, Group VIB metal compounds which are reducible by hydrogen to the corresponding elemental metal, or manganese or iron promoters. Specific examples of the group VIB metals or hydrogen-reducible metal compounds include elemental chromium, chromium acetate, chromium chloride, chromium oxide, elemental molybdenum, molybdenum hydroxide, molybdenum oxide, elemental tungsten, tungsten chloride, tungsten oxide, and the like, and mixtures of any two or more thereof. The weight ratio of the group VIB component to the metal component of the nickel or cobalt catalyst can be any suitable value, but will generally be in the range from about 0.001:1 to about 0.2:1 and preferably in the range from about 0.005:1 to about 0.1:1.

The catalysts can be in supported or unsupported form. Typical support materials include, for example, carbon, aluminium oxide, silicium dioxide, $Cr_2O_3$, titanium dioxide, zirconium dioxide, zinc oxide, calcium oxide, magnesium oxide, barium sulfate, calcium carbonate or aluminium phosphate. The nickel or cobalt catalyst can be bound on the substrate in an amount of, for example, about 1.0–20.0% by weight.

The preferred catalysts are Raney nickel and Raney cobalt catalysts. Such catalysts are, for example, formed by mixing nickel and aluminum or cobalt and aluminum and subsequently treating the respective mixtures with a suitable base, such as sodium hydroxide to remove the aluminum, thus leaving a highly reactive nickel or cobalt metal catalyst.

In all cases nickel catalysts are preferred; highly preferred are Raney nickel catalysts.

According to a preferred embodiment of the present invention the nickel or cobalt catalysts are pretreated with a carboxylic acid or a salt or an anhydride thereof or an ammonium salt, or a vanadium-, a tungsten-, or a molybdenum compound. Mixtures of at least two of these compounds can also be used.

Carboxylic acids, including polycarboxylic acids, having from 1 to 8 carbon atoms, especially 2 to 8 carbon atoms, are preferred. The carboxylic acids can be unsubstituted or substituted by, for example, hydroxy or halogen (like fluorine). Examples of such carboxylic acids are formic acid, acetic acid, propionic acid, butanoic acid, pentanoic acid, oxalic acid, malonic acid, succinic acid, maleic acid, malic acid, citric acid, tartaric acid, trifluoracetic acid. Examples for anhydrides are acetic anhydride, propionic anhydride and further anhydrides of the carboxylic acids mentioned above. Examples for salts of the carboxylic acids are the corresponding alkali metal salts, like sodium salts.

Preferred are carboxylic acids having from 2 to 4 carbon atoms, especially 2 carbon atoms. These carboxylic acids can be unsubstituted or substituted as given above. This definition should also include the salts and anhydrides thereof. Highly preferred is acetic acid (as well as the salts and the anhydride thereof).

Ammonium salts are, for example, ammonium halides, like ammonium chloride or especially ammonium fluoride.

Preferred vanadium compounds are those in which vanadium has the oxidation state 0, 2, 3, 4 or 5. Elemental vanadium is also suited. Examples of such compounds are $V_2O_5$, $VOCl_3$, $V_2O_4$, $NH_4VO_3$. Specially prefered are acetyl acetonate (acac) containing compounds, examples of such compounds are $V(acac)_3$, $VO(acac)_2$. The vanadium compounds are used in catalytic amounts, solved or dispersed.

Preferred tungsten or molybdenum compounds are compounds in which the metal has the oxidation state 0, 2, 3, 4, 5 or 6. Examples are $H_2WO_4$, $H_3[P(W_3O_{10})_4]$; $H_2MoO_4$, $H_3[P(Mo_3O_{10})_4]$.

For the pretreatment of the nickel or cobalt catalysts the use of carboxylic acids or salts or anhydrides thereof, or acetyl acetonate containing compounds is preferred. Highly preferred are carboxylic acids.

Advantageously the pretreatment is carried out in an aqueous medium. As a rule the aqueous medium contains the nickel or cobalt catalyst and the agent used for the treatment. Usually the treatment is carried out at ambient temperature, although also lower or higher temperatures can be used.

The reaction conditions of the hydrogenation, like time, temperature and pressure, are to a large extent interchangeable, as will be recognized by the skilled practitioner.

Preferably, the hydrogenation is carried out in an organic solvent, like an alcohol (for example methanol or especially ethanol). Furthermore, it is preferred that the hydrogenation is carried out in presence of a base (examples are $NH_3$, $NH_4OH$ and $NaOH$).

The cited catalysts can be present in the reaction mixture in an amount of about 0.1 to 500% by weight, preferably of 20 to 200% by weight, based on the amount of educt used.

The educts can be present in the reaction mixture in an amount of about 0.1 to 80% by weight, preferably of 5 to 20% by weight, based on the weight of the reaction mixture.

The temperature to be used for the reaction can be, for example, 0 to 200° C., a temperature of 20 to 120° C. being preferred. Highly preferred is a temperature of 20 to 80° C.

The reaction time can vary, for example, from 0.1 to 24 hours. Usually the reaction time is from 0.1 to 14 hours, especially from 0.1 to 4 hours.

The hydrogen pressure is, for example, 1 to 200 bar, especially 1 to 100 bar. A hydrogen pressure of 20 to 60 bar is preferred.

The catalyst can be re-used 1 to 100 times, especially 1 to 10 times; surprisingly, it is possible to re-use the catalyst without further treatment and the recycled catalyst shows no decrease in activity or selectivity.

After the reaction the product can be further purified according to known methods. For example, the product obtained after the reaction can be dissolved in an organic solvent (like diisopropyl ether) and separated by addition of an acid and filtration of the corresponding salt. Preferably, the product can be purified by addition of a hydrogen halide (like hydrogen chloride) or a carboxylic acid having from 1 to 6 carbon atoms (like formic acid). Highly preferred is the addition of formic acid after which the compound is separated by filtration as the compound of formula (1a)

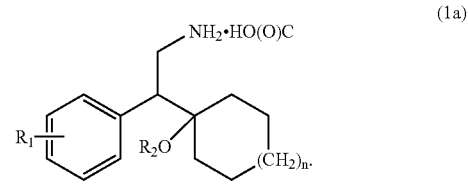

(1a)

A further object of the present invention are compounds of formula (1a). As to these compounds the meanings and preferences given above apply. The compounds of formula (1a) do not require special treatment when they are further converted into compounds of formula (3).

Alternatively, the product can be used directly, without purification, for further reactions like those described below.

Another object of the present invention is a process for the preparation of a compound of formula

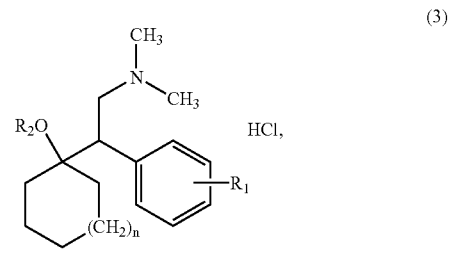

(3)

wherein $R_1$, $R_2$ and n are as defined above, comprising hydrogenating a compound of formula

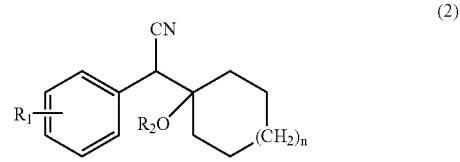

(2)

in the presence of a nickel or cobalt catalyst to give the compound of formula $$\text{(1)}$$

(Structure: R₁-phenyl, R₂O, CH₂NH₂, cyclohexane with (CH₂)ₙ)

and converting the compound of formula (1) to the compound of formula (3).

As to $R_1$, $R_2$ and n the above meanings and preferences apply.

The conversion of the compound of formula (1) to the compound of formula (3) can be carried out according to known processes. Such a conversion and the reaction conditions to be used are described in U.S. Pat. No. 4,535,186 (see especially Example 3).

In general, a method for such a conversion comprises the following steps:

$$\text{(1)} \xrightarrow{\text{N-methylation A)}} \text{(4)}$$

and B) preparation of the corresponding hydrochloride salts.

Step A) can, for example, be carried out by reaction of the compound of formula (1) with formaldehyde, formic acid in a large excess of water. Step B) can be carried out in conventional manner by forming the acid addition salt, whereby preferably an equimolar amount of hydrochloric is used.

According to the present invention the intermediates of formula (1) can be obtained in high yields. The use of expensive catalysts can be dispensed with.

The following examples illustrate the invention:

EXAMPLE 1 a) Pretreatment of the Catalyst 135 g of Raney nickel are washed three times each with 135 ml of water followed by 250 ml of an aqueous solution of acetic acid (5% by volume) and again three times each with 1000 ml of water.

b) Hydrogenation

A 5 liter autoclave is charged with 180 g of 1-[cyano(4-methoxyphenyl)methyl]cyclohexanol, 2400 ml of methanol, 600 ml of aqueous ammonia (25% by volume) and 135 g of Raney nickel (pretreated as given under 1a)) and the mixture is subjected to hydrogenation at 27 to 30° C. and 120 psi pressure of hydrogen for 9 to 10 hours. The reaction mixture is filtered through 100 g of the celite and the catalyst bed is washed with 700 ml of methanol. The filtrate is concentrated to get 167.1 g of the crude product as an oily residue. 1.1 g of the crude product is dissolved in 2 ml of dry ethyl acetate and about 2 ml of isopropanolic HCl are added (the pH of the solution is about 2). The solvent is removed at high vacuum to give 1.14 g of 1-[2-amino-1-(4-methoxyphenyl)ethyl]cyclohexanol hydrochloride.

EXAMPLE 2 a) Pretreatment of the Catalyst 50 ml of an aqueous solution of acetic acid (5% by volume) are added to 5 g of Raney nickel (suspension containing 60% by weight of the catalyst). The resulting suspension is stirred at ambient temperature for 10 to 15 minutes. After separation the catalyst is washed four times with deionised water.

b) Hydrogenation

An autoclave is charged with 1.2 g of 1-[cyano(4-methoxyphenyl)methyl]cyclohexanol, the amount of Raney nickel obtained after the pretreatment given above under 2a), 24 ml of ethanol and 6 ml of aqueous ammonia (25% by volume) and the mixture is subjected to hydrogenation at 60° C. and 40 bar pressure of hydrogen for 140 minutes. The catalyst is filtered off and washed with ethanol. The filtrate and the ethanol used to wash the catalyst are combined and concentrated by evaporation to get 1.2 g of the crude product as an oily residue. The crude product contains 79% by weight of 1-[2-amino-1-(4-methoxyphenyl)ethyl]cyclohexanol (HPLC). The crude product obtained as given above is dissolved in diisopropyl ether and HCl is added in order to form the HCl addition salt. The salt obtained is filtered off, washed with diisopropyl ether and dried in vacuum. 1.23 g of white crystals are obtained having a melting point of 169° C. and containing 84% by weight of 1-[2-amino-1-(4-methoxyphenyl)ethyl]cyclohexanol hydrochloride (HPLC).

EXAMPLE 3

Example 2 is repeated, using twice the amount of pretreated Raney nickel given in Example 2, carrying out the hydrogenation for 70 minutes instead of 140 minutes and dispensing with the formation of the HCl addition salt. 1.2 g of the crude product are obtained containing 86% by weight of 1-[2-amino-1-(4-methoxyphenyl)ethyl]cyclohexanol (HPLC).

EXAMPLE 4

Example 2 is repeated, using the same amount of Raney cobalt instead of Raney nickel, carrying out the hydrogenation for 90 minutes instead of 140 minutes and dispensing with the formation of the HCl addition salt. 1.2 g of the crude product are obtained containing 92% by weight of 1-[2-amino-1-(4-methoxyphenyl)ethyl]cyclohexanol (HPLC).

EXAMPLE 5 a) Pretreatment of the Catalyst

A saturated aqueous solution of V(acac)₃ [acac=acetyl acetonate] in 500 ml of deionised water is added to 50 g of Raney nickel (suspension containing 60% by weight of the catalyst). The resulting suspension is stirred at ambient temperature for 15 to 20 minutes. After separation the catalyst is washed five times with 500 ml of deionised water.

b) Hydrogenation

An autoclave is charged with 33 g of 1-[cyano(4-methoxyphenyl)methyl]cyclohexanol, the amount of Raney nickel catalyst obtained after the pretreatment given above under 5a), 320 ml of ethanol and 80 ml of aqueous ammonia (25% by volume) and the mixture is subjected to hydrogenation at 60° C. and 40 bar pressure of hydrogen for 640 minutes. The catalyst is filtered off and washed with ethanol. The filtrate and the ethanol used to wash the catalyst are combined and concentrated by evaporation to get 33 g of the crude product as an oily residue. The crude product contains 93% by weight of 1-[2-amino-1-(4-methoxyphenyl)ethyl]cyclohexanol (HPLC).

The crude product can be processed directly to give the corresponding HCl addition salt.

EXAMPLE 6 a) Pretreatment of the Catalyst 50 ml of an aqueous solution of $H_3[P(W_3O_{10})_4].xH_2O$ (0.5% by volume) is added to 5 g of Raney nickel (suspension containing 60% by weight of the catalyst). The resulting suspension is stirred at ambient temperature for 15 to 20 minutes. After separation the catalyst is washed five times with deionised water.

b) Hydrogenation

An autoclave is charged with 1.2 g of 1-[cyano(4-methoxyphenyl)methyl]cyclohexanol, the amount of Raney nickel obtained after the pretreatment given above under 6a), 24 ml of ethanol and 6 ml of aqueous ammonia (25% by volume) and the mixture is subjected to hydrogenation at 60° C. and 40 bar pressure of hydrogen for 300 minutes. The catalyst is filtered off and washed with ethanol. The filtrate and the ethanol used to wash the catalyst are combined and concentrated by evaporation to get 1.2 g of the crude product as an oily residue. The crude product contains 90% by weight of 1-[2-amino-1-(4-methoxyphenyl)ethyl]cyclohexanol (HPLC).

EXAMPLE 7 a) Formation of the 1-[2-amino-1-(methoxyphenyl)ethyl]cyclohexanol formic acid salt: 49.8 g of crude 1-[2-amino-1-(methoxyphenyl)ethyl]cyclohexanol from the nitrile hydrogenation was suspended in 250 ml ethylacetate and 12 ml formic acid (98–100%) were added in one portion. The mixture was heated to reflux under stirring and subsequently cooled down to room temperature. The product was filtered off, washed with 100 ml hexane and dried in vacuo, yielding 48.1 g (82%) of crude formiate salt.

b) Purification of the Formiate Salt:

The crude formiate salt was suspended in 1 l ethylacetate, heated to reflux for 1 hour, cooled to room temperature and filtered off. At this stage, the product has got already a much improved purity a shown by HPLC (>98%). The purification procedure was repeated one time and the final product was dried in vacuo at 40° C., giving 29.6 g product (50%) as white crystalls. The purity was determined by HPLC to be >98%.

EXAMPLE 8

Reductive methylation of 1-[2-amino-1-(methoxyphenyl)ethyl]cyclohexanol formic acid salt: 29.6 g of the formiate salt from above was mixed with 100 ml water, 17 ml formic acid (98–100%) and 26 ml formaldehyde (37%) and heated to reflux for 20 hours. The mixture was cooled to room temperature, acidified with 25 ml 4 N hydrochloride acid to pH <1 and extracted five times with 50 ml ethylacetate. The pH of the aqueous phase was adjusted to >12 with 30% aqueous sodium hydroxide and 150 ml toluene were added. The mixture was passed through a R3 filter, the phases were separated and the aqueous phase was again extracted with 50 ml toluene. The combined organic phases were washed with 100 ml water. Under stirring 30 ml 4.2 N hydrochloride acid in 1,4-dioxane were added over 5 minutes and the formed suspension was stirred for additional 1 hour. The product was filtered off, washed two times with 50 ml hexane and dried in vacuo at 40° C. yielding 26.9 g of the hydrochloride salt as white crystalls (86%), pure by HPLC.

EXAMPLE 9 a) Pretreatment of the Catalysts 6.00 kg Raney Nickel are placed in a 50 l steel autoclave. 40 l of water containing of 115.2 g VO(acac)$_2$ are added. The mixture is stirred for 30 minutes at room temperature. Then the aqueous phase is removed.

b) Hydrogenation 4.00 kg of 1-[cyano(4-methoxyphenyl)methyl]cyclohexanol] is suspended in 5 l EtOH and transferred to the autoclave containing the modified Raney Nickel. Then, 22 l of EtOH are added and the autoclave is closed and checked for leaks. After this, the 6 l of 25% NH$_4$OH in water are added through an addition port. Then the gases in the autoclave are displaced by nitrogen (3 times) and hydrogen (3 times). Then the autoclave is pressurized to 40 bar and the reaction is started by turning the stirrer on. The reaction mixture is heated to 60° C. in about 20 minutes and the reaction is continued for 2 hours at 60° C. Then the autoclave is cooled to room temperature, the hydrogen is displaced by nitrogen and the autoclave is opened. After filtration of the catalyst, the reaction mixture is evaporated to dryness. HPLC analysis shows a selectivity for the desired 1-[2-amino-1-(4-methoxyphenyl)ethyl]cyclohexanol] of 93% (HPLC).

EXAMPLE 10 a) Pretreatment of the Catalysts 22.5 g Raney Nickel are placed in a 300 ml steel autoclave equipped with a filtration frit. 220 ml of an aqueous solution saturated with V(acac)$_3$ is added and stirred during 30 minutes. After standing over night, the water is discharged through the frit and the catalysts is washed with 50 ml water and 3×50 ml EtOH.

b) Hydrogenation 15 g of 1-[cyano(4-methoxyphenyl)methyl]cyclohexanol] is suspended in 50 ml EtOH and transferred to the 0.3 l autoclave containing the modified Raney Nickel. Then, 50 ml of EtOH are added and the autoclave is closed and checked for leaks. After this, the 30 ml of 25% NH$_4$OH in water are added through an addition port. Then the gases in the autoclave are displaced by nitrogen (3 times) and hydrogen (3 times). Then the autoclave is pressurized to 42 bar and the reaction is started by turning the stirrer on. The reaction mixture is heated to 60° C. in about 20 minutes and the reaction is continued for 2 hours at 60° C. Then the autoclave is cooled to room temperature, the hydrogen is displaced by nitrogen and the autoclave is opened. After filtration of the catalyst, the reaction mixture is evaporated to dryness. HPLC analysis shows a selectivity for the desired 1-[2-amino-1-(4-methoxyphenyl)ethyl]cyclohexanol] of 86% (HPLC).

c) Hydrogenation: Catalyst Re-use

The catalyst from the experiment described above is washed with 50 ml EtOH, then, the hydrogenation experiment is repeated exactly as described above. The same reaction times are observed. HPLC analysis shows a selectivity for the desired 1-[2-amino-1-(4-methoxyphenyl)ethyl] cyclohexanol] of 85%. The selectivity observed in subsequent runs is between 85% and 87% (HPLC) and no noticeable catalyst deactivation is observed over four re-uses. The Vanadium content of the products is always <2 ppm, and the Nickel content varies between 1 and 3 ppm.

The invention claimed is:

1. A process for the preparation of a compound of formula

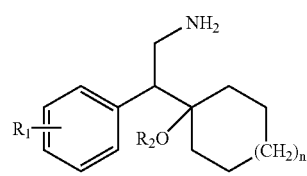

(1)

or salts thereof, wherein
$R_1$ is hydrogen, hydroxyl, or unsubstituted or substituted alkyl or alkoxy,
$R_2$ is hydrogen or a substituent which can be converted to hydrogen, and
n is 0, 1 or 2,
comprising hydrogenating a compound of formula

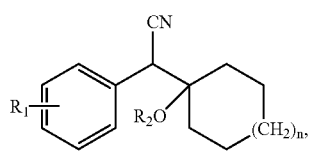

(2)

wherein $R_1$, $R_2$ and n are as defined above, in the presence of a nickel or cobalt catalyst, wherein the nickel or cobalt catalyst is pretreated with a compound selected from the group consisting of a carboxylic acid or a salt or an anhydride thereof, an ammonium salt, a vanadium compound, a tungsten compound, a molybdenum compound, and mixtures thereof.

2. A process according to claim 1, wherein $R_1$ is hydroxy or $C_1$–$C_4$alkoxy which is unsubstituted or substituted by phenyl.

3. A process according to claim 1, wherein $R_1$ is bonded in the para position.

4. A process according to claim 1, wherein $R_2$ is hydrogen, silyl, benzyl, formyl or $C_2$–$C_6$alkanoyl.

5. A process according to claim 1, wherein n is 1.

6. A process according to claim 1, wherein $R_1$ is methoxy, $R_2$ is hydrogen and n is 1.

7. A process according to claim 1, wherein a carboxylic acid having from 1 to 8 carbon atoms is used.

8. A process according to claim 1, wherein an acetyl acetonate containing vanadium compound is used.

9. A process according to claim 1, wherein the pretreatment is carried out in an aqueous medium.

10. A process according to claim 1, wherein the catalyst is Raney nickel or Raney cobalt.

11. A process according to claim 1, wherein a nickel catalyst is used.

12. A process according to claim 1, wherein the hydrogenation is carried out in the presence of an organic solvent.

13. A process according to claim 1, wherein a recycled catalyst is used.

14. A process according to claim 1, wherein after hydrogenation the product is purified by reaction with formic acid forming the compound of formula

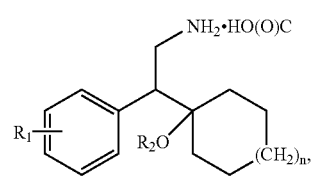

(1a)

wherein $R_1$, $R_2$ and n are as defined in claim 1.

15. A process for the preparation of a compound of formula

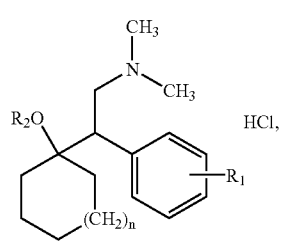

(3)

wherein
$R_1$ is hydrogen, hydroxyl, or unsubstituted or substituted alkyl or alkoxy,
$R_2$ is hydrogen or a substituent which can be converted to hydrogen, and
n is 0, 1 or 2,
comprising hydrogenating a compound of formula

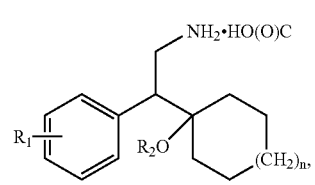

(1a)

wherein $R_1$, $R_2$ and n are as defined above, in the presence of a nickel or cobalt catalyst to give the compound of formula

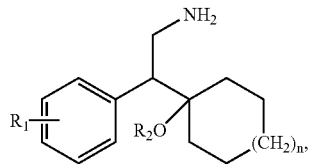 (1)

wherein $R_1$, $R_2$ and n are as defined above, and converting the compound of formula (1) to the compound of formula (3), wherein the nickel or cobalt catalyst is pretreated with a compound selected from the group consisting of a carboxylic acid or a salt or an anhydride thereof, an ammonium salt, a vanadium compound, a tungsten compound, a molybdenum compound, and mixtures thereof.

16. A process according to claim 15, wherein $R_1$ is methoxy, $R_2$ is hydrogen and n is 1.

* * * * *